(12) United States Patent
Isaacson et al.

(10) Patent No.: US 7,392,074 B2
(45) Date of Patent: Jun. 24, 2008

(54) SENSOR SYSTEM WITH MEMORY AND METHOD OF USING SAME

(75) Inventors: Philip O. Isaacson, Chanhassen, MN (US); Timothy L. Johnson, Plymouth, MN (US); Joe Raymond Crackel, Monticello, MN (US)

(73) Assignee: Nonin Medical, Inc., Plymouth, MN (US)

( * ) Notice: Subject to any disclaimer, the term of this patent is extended or adjusted under 35 U.S.C. 154(b) by 99 days.

(21) Appl. No.: 11/039,760

(22) Filed: Jan. 21, 2005

(65) Prior Publication Data

US 2006/0167351 A1    Jul. 27, 2006

(51) Int. Cl.
*A61B 5/1455* (2006.01)
(52) U.S. Cl. .................................. 600/310; 600/323
(58) Field of Classification Search ................. 600/309, 600/310, 323
See application file for complete search history.

(56) References Cited

U.S. PATENT DOCUMENTS

| | | | |
|---|---|---|---|
| 4,167,331 A | 9/1979 | Nielsen | |
| 4,825,872 A | 5/1989 | Tan et al. | |
| 4,942,877 A | 7/1990 | Sakai et al. | |
| RE33,643 E | 7/1991 | Isaacson et al. | |
| 5,058,588 A | 10/1991 | Kaestle | |
| 5,267,562 A | 12/1993 | Ukawa et al. | |
| 5,285,783 A | 2/1994 | Secker | |
| 5,337,744 A | 8/1994 | Branigan | |
| 5,490,523 A | 2/1996 | Isaacson et al. | |
| 5,800,349 A | 9/1998 | Isaacson et al. | |
| 5,807,247 A | 9/1998 | Merchant et al. | |
| 5,846,190 A | 12/1998 | Woehrle | |
| 5,891,021 A | 4/1999 | Dillon et al. | |
| 6,298,255 B1 | 10/2001 | Cordero et al. | |
| 6,397,091 B2 | 5/2002 | Diab et al. | |
| 6,584,336 B1 * | 6/2003 | Ali et al. ..................... | 600/323 |
| 6,591,123 B2 | 7/2003 | Fein et al. | |
| 6,600,940 B1 | 7/2003 | Fein et al. | |
| 6,628,975 B1 | 9/2003 | Fein et al. | |
| 6,708,049 B1 | 3/2004 | Berson et al. | |
| 6,760,610 B2 | 7/2004 | Tschupp et al. | |
| 6,801,797 B2 | 10/2004 | Mannheimer et al. | |
| 2002/0038081 A1* | 3/2002 | Fein et al. ................... | 600/323 |
| 2003/0195402 A1 | 10/2003 | Fein et al. | |
| 2004/0087845 A1* | 5/2004 | Katarow et al. ............. | 600/323 |

OTHER PUBLICATIONS

Datasheet on Reusable SpO2 Sensors, Koninklijke Philips Electronics N.V., Nov. 2003.

* cited by examiner

*Primary Examiner*—Eric F Winakur
*Assistant Examiner*—Etsub D Berhanu
(74) *Attorney, Agent, or Firm*—Fulbright & Jaworski L.L.P.

(57) ABSTRACT

A method of using an oximeter sensor assembly including the steps of detecting light from a light emitting element and storing digital data in a memory associated with the sensor assembly. The stored digital data includes coefficients for use by an oximeter monitor coupled to the sensor assembly to calculate data from the detected light, wherein the coefficients represent a combination of different sensor-specific characteristics, application-specific characteristics, and patient-specific characteristics. Control means including means for processing received information signals in accordance with the equation in response to received coefficients to determine blood oxygen levels is provided.

8 Claims, 2 Drawing Sheets

SENSOR SYSTEM WITH MEMORY AND METHOD OF USING SAME

FIELD OF THE INVENTION

The present invention relates generally to physiological sensors. More specifically, the present invention relates to a sensor assembly and system adapted to improve sensor utility by storing information representative of multiple characteristics of the sensor, patient and application within a memory of the sensor assembly.

BACKGROUND OF THE INVENTION

Non-invasive physiological monitoring is a common means for testing, detecting, and treating a physiological condition. Typically, non-invasive monitoring techniques such as pulse oximetry, electrocardiography (ECG), electroencephalography (EEG), and ultrasonic imaging, to name a few, require that a sensor be placed in direct contact with a patient undergoing the procedure.

Pulse oximetry involves the non-invasive monitoring of oxygen saturation level in blood-perfused tissue indicative of certain vascular conditions. Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured. Oxygen saturation may be calculated using some form of the classical absorption equation know as Beer's law.

The light passed through the tissue is typically selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

Known sensors include an optical oximeter probe which uses a pair of light emitting diodes (LEDs) to direct light through blood-perfused tissue, with a detector picking up light which has not been absorbed by the tissue. The operation depends upon knowing the wavelength of the LEDs. Since the wavelength of LEDs can vary, a coding resistor can be placed in the probe with the value of the resistor corresponding to the actual wavelength of at least one of the LEDs. When the oximeter instrument is turned on, it first applies a current to the coding resistor and measures the voltage to determine the value of the resistor and thus the value of the wavelength of the LED in the probe. U.S. Pat. No. 4,700,708 discloses such an encoding mechanism.

U.S. Pat. No. 5,259,381 recognizes that the coded value of the wavelength of the red LED provided by a coding resistor may be inaccurate, since the actual wavelength can vary with temperature. Accordingly, this patent teaches including a temperature sensor in the oximeter probe to measure the actual temperature. With the actual temperature, and the coded wavelength value, a look-up table can be consulted to determine the actual LED wavelength for that temperature.

Another method of storing coded information regarding the characteristics of the LEDs is shown in U.S. Pat. No. 4,942,877. This patent discloses using an EPROM memory to store digital information which can be provided in parallel or serially from the sensor probe to the remote oximeter. The memory is described as storing coefficients for the saturation equation, wavelength, subwavelength (secondary emission), half-width of wavelength spectrum emitted by LED, intensity of LEDS or ratio, and on time of LEDS (written by the processor).

Other examples of coding probe characteristics exist in other areas. Multiple calibration values are sometimes required, with this making the circuitry more complex or requiring many leads. In U.S. Pat. No. 4,446,715, assigned to Camino Laboratories, Inc., a number of resistors are used to provide coded information regarding the characteristics of a pressure transducer. U.S. Pat. No. 3,790,910 discloses another pressure transducer with a ROM storing characteristics of the individual transducer. U.S. Pat. No. 4,303,984 shows another probe with digital characterization information stored in a PROM, which is read serially using a shift register. Typically, the coding element is mounted in the probe itself. For instance, U.S. Pat. No. 4,621,643 shows the coding resistor mounted in the probe element itself. In addition, U.S. Pat. No. 5,246,003 shows the coding resistor being formed with a printed conductive material on the probe itself.

In some devices, an electrical connector coupled by a cable to a device attached to a patient may include a coding element. For example, U.S. Pat. No. 3,720,199 shows an intra-aortic balloon catheter with a connector between the catheter and a console. The connector includes a resistor with a value chosen to reflect the volumetric displacement of the particular balloon. U.S. Pat. No. 4,684,245 discloses a fiber optic catheter with a module between the fiber optic and electrical wires connected to a processor. The module converts the light signals into electrical signals, and includes a memory storing calibration signals so the module and catheter can be disconnected from the processor and used with a different processor without requiring a recalibration.

U.S. Pat. No. 5,645,059 teaches using a modulated signal to provide the coded data to a remote analyzer. U.S. Pat. No. 5,429,129 shows using a voltage regulator to produce a specific voltage value in response to an attempt to read by the analyzer.

U.S. Pat. No. 5,058,588 teaches an oximeter sensor with an encoding element that could be resistor, ROM, or customized integrated circuit. The encoding element encodes the type of sensor (in particular, type indicating area of placement on body—finger, ear, foot, arm; also, the type of sensor can indicate transmission/reflection type, or adult/neonate (indicating correction to be performed on theoretical oxygen saturation, allow switching between physiological limits such as minimum/maximum pulse rates for adults/neonates); the maximum driving current may be adapted according to type of sensor, and contact of sensor with tissue can be tested by means of an attenuation measurement if sensor type is known).

U.S. Pat. No. 5,645,059, the disclosure of which is hereby incorporated herein by reference, teaches coding information in sensor memory used to provide pulse modulated signal, to indicate the type of sensor (finger, nose), the wavelength of a second LED, the number of LEDs, the numerical correction terms to the standard curves, and an identifier of the manufacturer.

A number of catheter patents also discuss encoding information in the catheter. Sentron U.S. Pat. No. 4,858,615 teaches encoding the type of sensor, type number, serial number, date of production, safe use life of the sensor, correction data for non-linearity, pressure sensitivity, offset, and temperature sensitivity.

Interflo Medical Published PCT Application No. PCT/US92/08263, Publication No. WO 93/06776 teaches encoding patient specific data, size, manufacture date, batch number, sterilization date, expiration date, transducer number and type, manufacturer's name and address, thermistor heating element resistance, filament efficiency, program segments or patient historical data, format version for the calibration data, trademark information, catheter unique serial number, ship date, other date and time information, security code to identify manufacturer, thermal mass, filament composition, coefficient of resistance, layout byte, checksum, copyright, number of seconds since a certain date, patient weight, patient height, timestamp of data point, and a count of all CO data points in EEPROM.

U.S. Pat. No. 5,162,725 describes storing both calibration and ID information in a sensor memory. U.S. Pat. No. 5,016,198 describes a coding memory in a sensor with data for defining sensor's characteristic curve. U.S. Pat. No. 4,303,984 describes a memory which stores characterization information, such as linearization information for a pressure sensor. U.S. Pat. No. 5,365,462 describes a date code in a sensor memory. U.S. Pat. No. 4,734,873 describes a pressure sensor with a PROM storing coefficients for a polynomial. U.S. Pat. No. 4,845,649 describes a PROM in a sensor storing correcting data. U.S. Pat. No. 5,070,732 shows calibration data in a sensor memory. U.S. Pat. No. 5,720,293 talks about different calibration information for a catheter, including a security code (encryption is discussed), serial number, model number, ID data such as calibration, manufacture, sterilization and ship date or other date and time information, a software program segment, security code for identifying whether sensor made by same manufacturer as monitor manufacturer, filament or transducer resistance, heat transfer coefficient, thermal mass, filament composition and coefficient of resistance, layout byte, copyright notice, checksum, random data bytes. U.S. Pat. No. 5,008,843 describes a sensor with EEPROM ID and characteristics data.

The prior art does not disclose a sensor assembly which stores coefficients for a saturation or similar equation wherein the coefficients are defined as a combination of different sensor-specific characteristics, application-specific characteristics, and patient-specific characteristics. As detailed herein, the benefits of storing coefficients which comprehensively include a variety of different characteristics include improved sensor accuracy, system flexibility and the ability to utilize updated sensors with existing monitoring equipment.

Consequently, there is a need in the art for a sensor assembly which is capable of storing equation coefficients which represent a plurality of different characteristics including sensor-specific characteristics, application-specific characteristics, and patient-specific characteristics.

BRIEF SUMMARY OF THE INVENTION

The present invention is directed to a sensor system which provides, among other benefits, improved measurement accuracy and system flexibility. In one embodiment, the sensor assembly includes a portable sensor and a memory element. The portable sensor can include many known sensors used for the monitoring of physiological parameters.

In one embodiment of the invention, the memory element stores equation coefficients used in the process to determine a physiologic measurement. For example, the equation coefficients may be utilized to determine blood oxygen levels using well known blood oxygen saturation equations. The coefficients represent a combination of many different characteristics, including but not limited to: sensor-specific characteristics, application-specific characteristics and patient-specific characteristics, referred herein in combined form as SAP-specific characteristics.

In one embodiment, the coefficients defined by the SAP-specific characteristics are stored in a memory on the portable sensor and are communicated to a monitor for subsequent processing with a predetermined equation accessed by the monitor. The predetermined equation may be stored within a memory element of the monitor or otherwise communicated to the monitor.

In another embodiment of the present invention, the coefficients defined by the SAP-specific characteristics along with an associated equation are stored in a memory of the portable sensor. Both the coefficients and equation are communicated to a monitor for subsequent processing.

In yet another embodiment of the present invention, the coefficients defined by the SAP-specific characteristics along with an associated equation are stored in a memory of the portable sensor and are communicated to a processor within the sensor assembly. The internal processor is provided in communication with the monitor and may receive commands to initiate computations and transmit processed physiologic measurement to a monitor for subsequent display and/or storage.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS AND FIGURES

For purposes of facilitating and understanding the subject matter sought to be protected, there is illustrated in the accompanying drawings an embodiment thereof. From an inspection of the drawings, when considered in connection with the following description, the subject matter sought to be protected, its construction and operation, and many of its advantages should be readily understood and appreciated.

DETAILED DESCRIPTION OF THE PREFERRED EMBODIMENTS

For the purposes of explanation only, the present invention is disclosed utilizing an embodiment that is configured for the measurement of oxygen saturation through known oximetric transmittance techniques. As one skilled in the art can readily appreciate, the present invention is easily adaptable to accommodate a number of different physiological monitoring applications and configurations, including but not limited to, other optical sensors, reflective sensor, etc.

Figure 1:
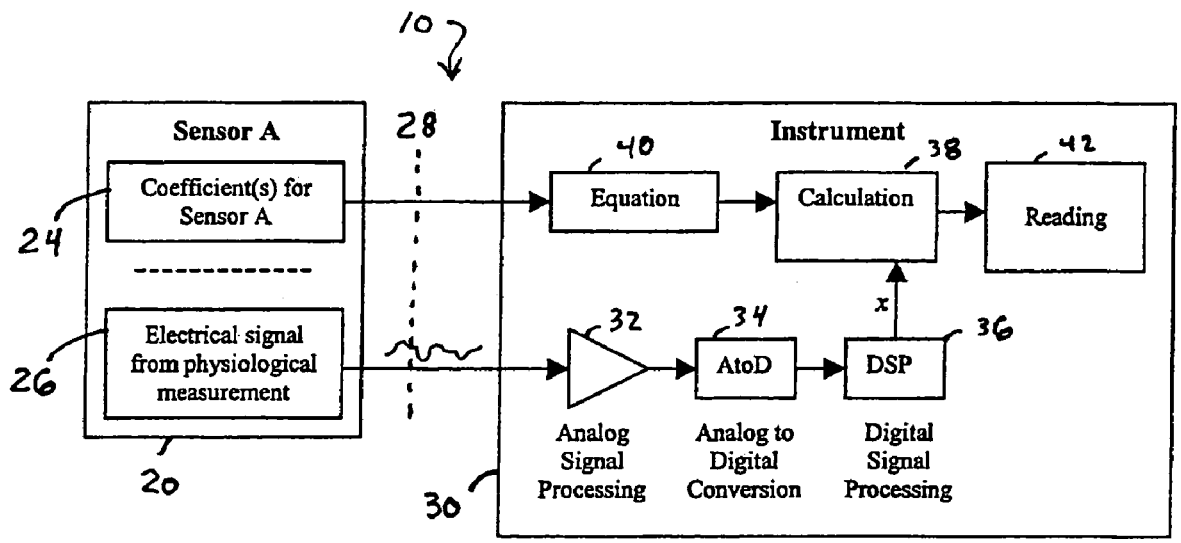
FIG. 1 is a block diagram of a first embodiment of a sensor system according to the present invention.

FIG. 1 illustrates an embodiment of a sensor system 10, including a sensor assembly 20 and sensor monitor 30 adapted as an electro-optical blood oxygen saturation sensor for a fingertip. In the illustrated embodiments, sensor assembly 20 is utilized within a system including a monitoring unit for oxygen saturation measurement. A variety of different sensor assemblies can be utilized to practice the present invention. For example, the sensor assembly 20 may includes a molded polymeric body and sensor holder, such as disclosed in U.S. Ser. No. 10/988,040, entitled Sensor Assembly, assigned to the present assignee, and incorporated by reference herein. Sensor assembly 20 may include an oximetric sensor having one or more LED's and one or more photodetectors and being connected to the monitoring unit via a lead wire. The sensor assembly 20 can also or alternatively contain other known components utilized in the measurement of oxygen saturation. Pulse oximeter systems are disclosed in U.S. Pat. Nos. 5,490,523, 5,800,349, and Re. 33643, all to Isaacson et al, and all assigned to the present assignee, Nonin Medical, Inc.

Sensor assembly 20 of FIG. 1 includes a memory element 24 and a sensor 26 which provides a signal to the sensor monitor 30 via line 28. Sensor 26 may include an oximetric sensor having one or more LED's and one or more photodetectors. Alternatively, sensor 26 may include other sensors for the measurement of physiological parameters such as oxygen or carbon dioxide in the blood, a measuring apparatus for the measurement of the carbon dioxide content, an optical measuring apparatus with means for the pulse oximetric measurement of the arterial oxygen saturation comprising an LED and a photodetector, a measuring apparatus for the measurement of the pulse frequency, a measuring apparatus for the measurement of the hematocrit (HCT), a measuring apparatus for the measurement of the blood pressure (CNIBP), a measuring apparatus for the measurement of components of the respiratory gas, a measuring apparatus for the measurement of the body temperature, and a measuring apparatus for the measurement of the moisture content. In addition, sensor 26 be used to measure certain other physiologic parameters as would be appreciated by those of ordinary skill in the relevant art. Sensor 26 may include digital or analog signal components or both.

Memory 24 may include digital and/or analog memory structures, including but not limited to random access memory (RAM), a FLASH memory, a programmable read only memory (PROM), an electrically erasable PROM, any kind of erasable memory, a write once memory, or other memory technologies capable of write operations. Analog memory structures may include, for example, a simple resistor network such as disclosed in the prior art referenced in the Brief Summary of the Invention.

Referring still to FIG. 1, sensor monitor 30 includes an analog signal processing element 32, an analog to digital conversion element 34, a digital signal processing element 36, a processor 38, a memory element 40 and a storage or display element 42 to provide information relating to the measured physiological parameter. One or more of these various elements of sensor monitor 30 may be implemented in hardware, software or a combination of hardware and software. Those of ordinary skill in the art will appreciate that various additional elements and/or components may be included in a functional system or that elements of sensor monitor 30 may be unnecessary or optional.

Sensor monitor 30 is in communication with sensor assembly 20 via line 28. The connection between sensor monitor 30 and sensor assembly can be by wireless telemetry, a cell phone data transmittal protocol, or via known electronic communication systems. Line 28 may communicate digital or analog signals or both. Line 28 may comprise a combination of hard lines and wireless channels. Line 28 may represent telemetry line(s) operating via FM or PCM/FM modulation. Alternative wireless technologies may also be applicable to communicate information between sensor assembly 20 and sensor monitor 30.

Memory 24 of sensor 20 stores equation coefficients used in the process to determine a physiologic measurement. In the example of FIG. 1, the equation coefficients are utilized to determine blood oxygen levels. The coefficients represent a combination of multiple different characteristics, including but not limited to sensor-specific characteristics, application-specific characteristics and patient-specific characteristics. As used herein, the term "coefficients" is broadly defined and includes parameters.

Sensor-Specific Characteristics Include:
Spectral characteristics of the light emitting element(s), such as wavelength, intensity, spectral bandwidth and secondary emissions.
Light emitting element parameters such as drive level, LED spacing, LED orientation relative to other components of the sensor assembly, collimation of light to tissue site, area of illumination at tissue site.
light detecting element characteristics, such response non-linearities, spectral response, area of detection at tissue site, collimation of light from tissue site.
sensor type, such as whether the sensor functions as a transmissive or reflective sensor or both.
sensor pressure relating to the compressive force applied to the tissue site by the mechanical structure of the sensor,
sensor light transmissive or reflective characteristics relating to materials of construction, such as whether the sensor is colored, opaque, translucent, etc.
alignment between light emitting element and light detecting element, e.g., offset or aligned.

Application-Specific Characteristics Include:
location of the sensor upon the patient, for example, whether the sensor is secured at an extremity or some other location of the patient, degree of perfusion at sampled tissue site relative to other tissue sites.
alignment of the sensor element(s) relative to the patient, for example, whether the sensor elements are parallely or transversly aligned relative to the longitudinal direction of a finger.
sensor displacement during use, for example, some sensors are more likely to be subject to displacement forces during use which may corrupt the measured physiologic signal.
sensor temperature during use.

the effects of external light sources, such as interference from sunlight or other external light sources.

Patient-Specific Characteristics Include:
patient age
gender of patient
patient size (neonate, pediatric, juvenile, adult applications)
medical conditions of patient
skin color
patient species information (human, veterinary application, etc.)

The above referenced sensor-specific, application-specific, and patient-specific characteristics include many known factors which may each influence the coefficients stored in sensor assembly memory 24. The above identified examples of characteristics are not meant to be a comprehensive collection. Other known or subsequently discovered characteristics may be utilized to determine the coefficients of the sensor system according to the present invention. In this regard, the stored coefficients represent a combination of the plurality of different characteristics.

Figure 2:
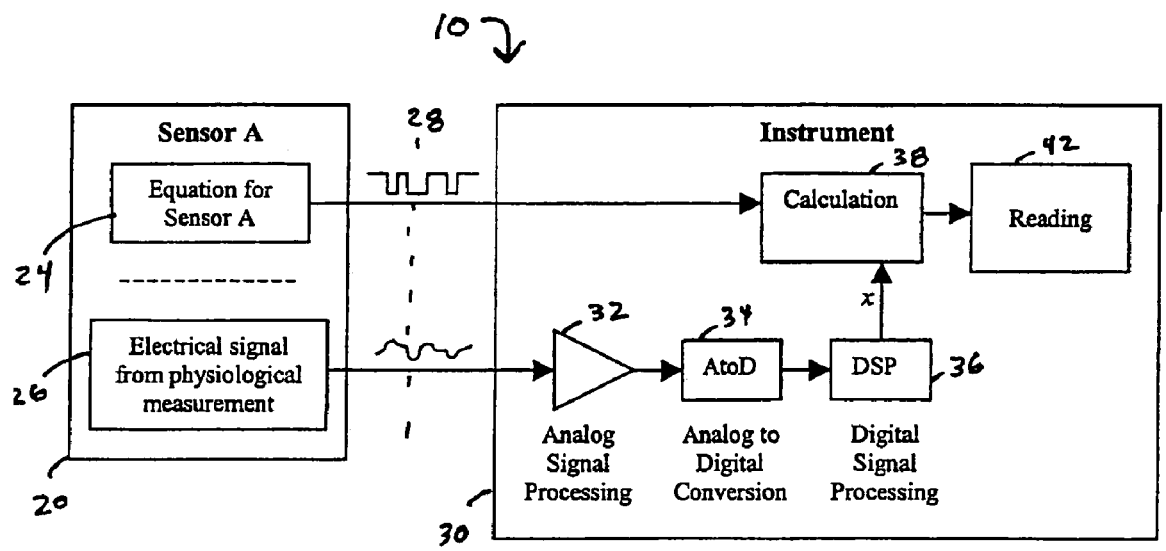
FIG. 2 is a block diagram of a second embodiment of a sensor system according to the present invention.

FIG. 2 illustrates another embodiment of the present invention wherein a calibration equation including calibration coefficients is stored in memory element 24. In use, the equation is communicated to the sensor monitor 30 and is used to calculate the physiologic parameter based on the received signal from sensor 26. The equations stored in memory element 24 may include polynomials, logarithmics, exponentials, or power-type equations. In this regard an optimally appropriate equation and calibration coefficients can be communicated to the sensor monitor 30, resulting in improved accuracy and flexibility. As used herein, the term "equation" is broadly defined and includes functions and algorithms.

Figure 3:
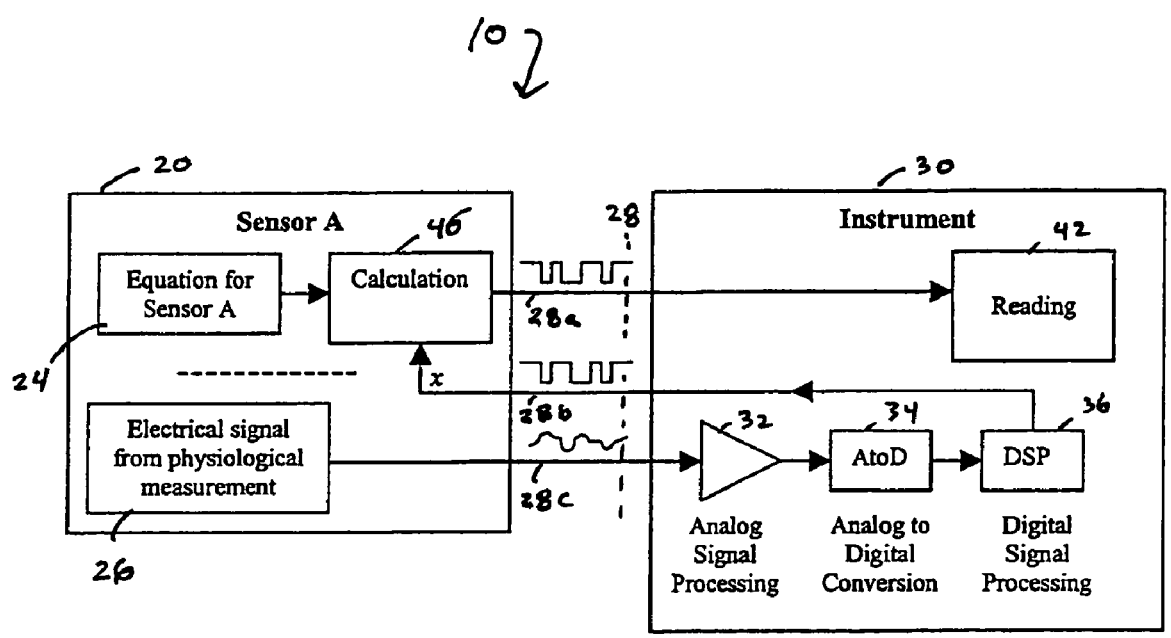
FIG. 3 is a block diagram of a third embodiment of a sensor system according to the present invention.

FIG. 3 illustrates yet another embodiment of the present invention wherein a calibration equation including calibration coefficients is stored in memory element 24. In addition, sensor 20 includes a sensor processor 46 for processing data from sensor 26 with reference to the stored calibration equation and coefficients. Sensor processor 46 and memory element 24 may be discrete elements or may be combined within a single device, such as programmable logic controller, or another electronic device as appreciated by those of ordinary skill in the relevant arts. As illustrated in FIG. 3, a preprocessed physiological measurement signal (x) is sent to sensor processor 46 via line 28b. The preprocessed signal (x) is a function of the electrical signal from the physiologic measurement of sensor 26 which is communicated to monitor 30 via line 28c. The preprocessed signal (x) may include amplitude information for a red light signal and for an infrared light signal. In another embodiment, the preprocessed signal (x) may include time derivative information of the red and infrared light signals from sensor 26. Sensor processor 46 calculates a blood oxygen saturation or other measurement based on the preprocessed signal (x) and the stored calibration equation and coefficients and communicates the information via line 28a to the oximeter monitor 30 for subsequent storage and/or display. Such an embodiment of the present invention may yield an improvement in sensor flexibility and accuracy of the reading. Processor 46 may include a microcontroller with memory or a microprocessor and interfaces on a single chip. Other processor 46 technologies may also be applicable to embodiments of the present invention.

Signals lines 28 represent communication paths between sensor 20 and monitor 30. Communication may be via analog communication and/or digital communication. Signal lines 28 may be represented by one or more discrete conductors. Signal lines 28 may represent wireless communication between sensor 20 and monitor 30. Bidirectional communication over a single line may require additional electronic components, such as multiplexors, etc. Those of ordinary skill in the relevant arts would appreciate that a variety of different communication approaches may be utilized to practice the present invention. For example, the signal line 28 associated with sensor 26 may be an analog channel. In another embodiment, the signal line 28 associated with sensor 26 may be a digital channel with appropriate analog-to-digital conversion being handled within sensor 20.

It may be necessary to update the calibration coefficients stored within memory element 24 as technology progresses and the operating parameters are refined or changed. Because sensor 20 would typically be much less expensive to replace than the system monitor 30, it is desirable to provide data corresponding to the updated coefficients in the sensors rather than in the sensor monitors.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, device, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A physiologic signal processing method comprising:
emitting light from a light emitting element on a sensor;
detecting light with a light detecting element on the sensor;
storing information on a memory on the sensor, said information including coefficients used to determine physiologic measurements based upon light signals received from the light detecting element, said coefficients being derived as a combination of different sensor-specific characteristics, application-specific characteristics, and patient-specific characteristics, said information also including an equation for use to compute a physiologic parameter;
determining a preprocessed signal at a remote monitor said preprocessed signal being derived from an electrical signal from the light detecting element;
communicating said preprocessed signal from said monitor to said sensor; and
with a processor on said sensor, determining said physiologic measurements based upon the preprocessed signal, the coefficients and the equation information.

2. The physiologic signal method of claim 1 wherein the preprocessed signal includes information relating to an amplitude of a detected light signal.

3. The physiologic signal method of claim 2 wherein the preprocessed signal includes a red light amplitude and an infrared light amplitude.

4. The physiologic signal method of claim 2 wherein the preprocessed signal includes time derivatives of a received red light signal or infrared light signal or both.

5. The physiologic signal method of claim 1 wherein the physiologic measurements are blood oxygen levels.

6. The method of claim 1 wherein the different sensor-specific characteristics include one or more of: light emitting element characteristics, light detecting element characteristics, sensor pressure, sensor type, sensor color and sensor materials of construction.

7. The method of claim 1 wherein the different application-specific characteristics include one or more of: location of sensor upon the patient during use, alignment of the sensor relative to the patient during use, sensor displacement during use, sensor temperature during use, and the effects from external light sources.

8. The method of claim 1 wherein the different patient-specific characteristics include one or more of: age, gender, medical conditions of patient, skin color, and patient species information.

\* \* \* \* \*